United States Patent [19]

Girard

[11] Patent Number: 4,537,697

[45] Date of Patent: Aug. 27, 1985

[54] METHOD OF ENHANCING SOLUBILITY OF HALOGENATED HYDANTOINS

[75] Inventor: Theodore A. Girard, Williamsport, Pa.

[73] Assignee: Glyco, Inc., Norwalk, Conn.

[21] Appl. No.: 562,088

[22] Filed: Dec. 16, 1983

[51] Int. Cl.$^3$ .................. C11D 7/54; C11D 17/00
[52] U.S. Cl. ............................ 252/90; 4/227;
4/228; 134/2; 134/22.16; 134/22.17; 252/89.1;
252/102; 252/103; 252/174; 252/174.14;
252/187.33; 252/363.5
[58] Field of Search ............... 134/2, 22.16, 22.17,
134/22.19; 252/90, 102, 174, 174.14, 187.2,
187.33, 363.5, 89.1, 103; 548/311; 4/227, 228

[56] References Cited

U.S. PATENT DOCUMENTS

| | | | |
|---|---|---|---|
| 2,422,255 | 6/1947 | Peters | 252/187.33 X |
| 2,779,764 | 1/1957 | Paterson | 548/311 |
| 2,795,556 | 6/1957 | Quinn | 252/187.33 |
| 2,798,875 | 7/1957 | Scheer et al. | 548/311 |
| 2,863,800 | 12/1958 | Gottfried | 252/363.5 X |
| 2,938,764 | 5/1960 | Blomfield | 252/187.33 X |
| 3,142,647 | 7/1964 | Glasgow | 252/363.5 X |
| 4,011,172 | 3/1977 | Marsan et al. | 252/187 R |
| 4,116,849 | 9/1978 | Leikhim | 252/103 |
| 4,116,851 | 9/1978 | Rupe et al. | 252/103 |
| 4,208,747 | 6/1980 | Dirksing . | |
| 4,242,216 | 12/1980 | Daugherty et al. | 252/103 |
| 4,289,640 | 9/1981 | Falivene | 252/95 |
| 4,308,625 | 1/1982 | Kitko . | |
| 4,347,153 | 8/1982 | Hooper et al. | 252/174.25 |
| 4,353,866 | 10/1982 | Wong . | |
| 4,469,848 | 9/1984 | Hooper et al. | 252/106 |

Primary Examiner—Marc L. Caroff
Attorney, Agent, or Firm—Cushman, Darby & Cushman

[57] ABSTRACT

The generation of total and free halogen in aqueous solutions of halogenated hydantoins is potentiated by the use of a solubility agent selected from the group consisting of magnesium oxide, barium hydroxide, sodium carbonate, 5,5-dialkyl substituted hydantoin and mixtures thereof. The use of these solubility agents in combination with halogenated hydantoins, such as bromochloromethylethylhydantoin, is especially suitable for use as a toilet bowl cleaner.

23 Claims, No Drawings

METHOD OF ENHANCING SOLUBILITY OF HALOGENATED HYDANTOINS

BACKGROUND OF THE INVENTION

The present invention relates to the enchanced solubility of halogenated hydantoins in aqueous solutions by the addition thereto of a solubility agent selected from the group consisting of magnesium oxide, barium hydroxide, sodium bicarbonate, sodium carbonate, 5,5-dialkyl substituted hydantoins and mixtures thereof which agent increases the level of both free and total halogen in solution. The enchanced solubility of such materials renders them particularly suitable for use in toilet bowl applications.

The halogenation of hydantoins results in substitution at the $N_1$ and $N_3$ positions as shown in the following equation:

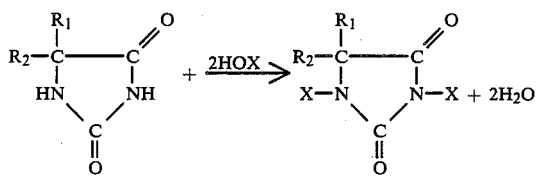

X=Chlorine or bromine; $R_1$, $R_2$=$CH_3$—and/or $CH_3CH_2$—.

Typical "hydantoins" are, for example, 5,5-dimethylhydantoin, 5-ethyl-5-methyl-hydantoin, 5,5-diethylhydantoin whose substitution in the 5-position is a function of the ketone used in synthesizing the "hydantoin" by the classical Bucherer-Bergs reaction.

A number of halogenated hydantoins are well-known for their bleaching and disinfecting properties. Their effectiveness in these applications is due to their ability to generate (release) positive halogen in aqueous solution.

In many applications, it is desirable to formulate the halogenated hydantoin in a shape retentive form, i.e., as a granule, tablet or briquette due to the inherently irritating and dusty nature of the compounds.

Halogenated derivatives of dimethylhydantoin (e.g. 1,3-dibromo-5,5-dimethylhydantoin; 1-bromo-3-chloro-5,5-dimethylhydantoin and 1,3-dichloro-5,5-dimethylhydantoin) are halogen donors typically utilized for various purposes. Thus, 1-bromo-3-chloro-5,5-dimethylhydantoin is used for swimming pool sanitizers, while 1,3-dichloro-5,5-dimethylhydantoin has been used successfully for bleaching (see, Kirk-Othmer, Encyclopedia of Chemical Technology, Volume 12, pp. 704–705, Wiley Interscience, 1980; and U.S. Pat. No. 2,779,764 to Patterson).

Halogenated derivatives of dimethylhydantoin are fine, dusty powders which are difficult to compact into solid forms of high integrity or to granulate. Compaction of 1,3-dichloro-5,5-dimethylhydantoin has been proposed in U.S. Pat. No. 4,242,216 to Daugherty et al. Recently, in my co-pending application Ser. No. 465,175 filed Feb. 9, 1983, titled "Halogenated Hydantoins" substantially dust-free, free flowing and compactible halogenated methylethyl hydantoins are described.

Halogenated hydantoins are potentially useful in a wide variety of applications which heretofore have been primarily serviced through the use of hypohalite bleaches such as sodium hypochlorite and the like. Such applications include:
fabric bleaching;
swimming pool disinfection;
spa or hot tub disinfection;
water cooling tower disinfection;
automatic dishwasher-bleaching; and
toilet bowl cleaners.

These applications, however, require the generation of controlled concentrations of "free" halogen. Commercially used halohydantoins generally are in the form of hard compressed tablets and briquettes having a relatively low surface area. Such solid halohydantoins do not dissolve as rapidly as the powder or granules, and in many applications it is desirable to achieve enhanced solubility of the halohydantoins.

Accordingly, it is a primary object of the present invention to provide a means for controlling the concentration of free halogen in aqueous solutions of halohydantoins.

It is a further object of the present invention to provide method for increasing the rate of dissolution of halogenated hydantoins.

A still further object of the present invention is to provide an enhanced method and composition for the cleaning and disinfection of toilet bowls.

These and other objects will be more apparent from the following discussion.

SUMMARY AND DETAILED DESCRIPTION OF THE INVENTION

In accordance with the present invention, it has been found that the rate of solubility of halogenated hydantoins in aqueous solutions is surprisingly increased by the addition of a relatively small amount of a solubilizing agent selected from the group consisting of magnesium oxide, barium hydroxide, sodium bicarbonate, sodium carbonate, 5,5-dialkylsubstituted hydantoins, and mixtures thereof. Addition of the solubilizing agent results in increasing the level of both total and free halogen in the resulting aqueous solution. Thus, according to one embodiment of the invention there is provided a composition which comprises a halogenated hydantoin of the formula:

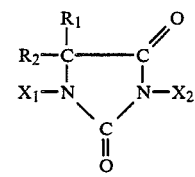

wherein $X_1$ and $X_2$ independently are chlorine or bromine. $R_1$ and $R_2$ independently are methyl or ethyl; and a solubilizing agent such as magnesium oxide which is present in an amount sufficient to increase the amount of total and free halogen of the composition when placed in an aqueous environment.

The physical form of the composition is not critical since the use of combined solubilizing agent and halogenated hydantoin can increase the concentration of halogen in an aqueous environment by 30 percent or more regardless of whether the composition is in powder, granule, tablet or briquette form. In any form the rate at which equilibrium value is reached for both the total and free chlorine of the halohydantoin is increased by addition of the solubilizing agent. However, little, if any effect on the equilibrium value of total and free halogen was observed.

The use of dibromo- or a bromochloro alkyl hydantoin has been found to offer a higher concentration (if desired) of "free" halogen than the corresponding dichloro material. A further advantage to the use of bromochloro alkylhydantoin is the regeneration of $Br^+$ at the expense of the less readily hydrolyzed $Cl^+$.

In addition to providing for an appropriate level of halogen, it is also desirable in many instances that the halogenated hydantoin be capable of being readily processed into "forms" such as tablets, rods, briquettes, sticks, and the like. The composition selected for a given application should be capable of being converted to such forms by conventional equipment such as compacting rolls and tableting apparatus well known industrially. The forms should be hard, dust-free, stable chemically, and resist breakage during shipment. In contact with water, they should maintain their structural integrity and dissolve during use smoothly and evenly without becoming "mush", or fracturing. I have been unable to achieve this objective with any of the halogenated dimethylhydantoins. The physical properties of the halogenated dimethylhydantoin-crystal structure, static charge, etc. cause it to be resistant to attempts, with and without additives, to be mechanically shaped by compression into useful forms as defined above. However, as disclosed in copending application Ser. No. 465,175, noted above, the halogenated 5-ethyl-5-methylhydantoins are readily compactible into useful forms. The "formability" properties of halogenated methylhydantoins are so unusual that high levels of the halogenated dimethylhydantoins may be used in admixture and the "formability" characteristics retained.

Preferred halogenated hydantoins of the present invention are those of 1-bromo-3-chloro-5-ethyl-5-methylhydantoin (BCMEH). BCMEH lends itself to those certain applications (particularly toilet bowl cleansing and disinfection) where it is advantageous to increase the rate at which total and free halogen (expressed herein as total $Cl^+$ and free $Cl^+$) are generated before reaching an equilibrium concentration.

As noted above, the solubilizing agent should be present in an amount sufficient to increase the rate of solubility of the active halogenated hydantoin ingredient when present in solution in the absence of the agent. In the case of magnesium oxide, barium hydroxide, sodium bicarbonate, and sodium carbonate generally from about 0.5 to 10 percent (and preferably from about 1 to about 5 percent, especially about 2.5 percent) by weight of the solubilizing agent is satisfactory. Magnesium oxide is an especially preferred solubilizing agent.

The 5,5-dialkylsubstituted hydantoin when utilized as a solubilizing agent can be used in an amount up to an equimolar amount based on the halogenated hydantoin, but generally an amount up to about 25 percent by weight of the composition is sufficient (with from about 5 to about 20 percent by weight being preferred). While 5,5-substitution with alkyl groupings containing from 1 to 6 carbons is suitable, it is preferred to utilize the methyl and ethyl substituted materials. Thus, the use of 5,5-dimethylhydantoin (DMH), 5,5-diethylhydantoin (DEH) and 5-methyl-5-ethylhydantoin (MEH) are preferred.

The various solubilizing agents may be added singly or in combination to the halogenated hydantoin materials to achieve a satisfactory increase in the rate of solubility of the halogenated hydantoin.

According to a further embodiment of the present invention there is provided a method for the cleansing and/or disinfection of a flush toilet, such as those conventionally equipped with a holding tank reservoir for delivering water to the toilet bowl. The compositions herein may be used in a manner well known in the art for delivery of dosage amounts of desired cleanser (typically, hypohalites heretofor) to the toilet bowl. Such cleansers and dispensing materials are well known as evidenced by the disclosure of Wong U.S. Pat. No. 4,353,866; Kito U.S. Pat. No. 4,308,625 and Dirksing U.S. Pat. No. 4,208,747, the entire disclosure of each being incorporated herein by reference. The compositions of the present invention when used for toilet bowl cleansing and/or disinfection are effective for extended flushes and provide an adequate level of bleaching. Furthermore, the compositions of the invention may be used in conjuction with other conventional additives found in compositions for sanitizing toilets such as dyes as disclosed in the aforementioned U.S. Pat. Nos. 4,308,625 and 4,353,866.

Indeed, the compositions of the present invention provide for an improved passive dosing dispenser (i.e. automatically dispensed toilet bowl cleaning and/or sanitizing products) designed for placement in the reservoir of a toilet as described for example in the aforementioned U.S. Pat. Nos. 4,353,866; 4,308,625; and 4,208,747. Conventional dispensers basically provide a dispensing means for a solid composition which is soluble in water to the extent necessary to achieve effective cleansing and/or disinfecting of the toilet bowl when dispensed during flushing of the toilet. Use of the compositions of the present invention in such dispensers for toilet bowl sanitation offers the advantage of not only providing a high and effective level of halogen, but at the same time minimizing offensive odor and corrosion.

As will be appreciated the present invention provides an effective means for increasing the level of free and total halogen in an aqueous solution of halohydantoin.

The following examples are offered to illustrate the various embodiments of the present invention but are not to be construed as limiting the scope thereof.

EXAMPLE ONE

Control of Free Halogen Content

The concentration of free halogen obtainable in aqueous solution can be controlled by increasing or decreasing the degree of bromine substitution in the 5,5-dialkylhydantoin ring. In a series of experiments, the halogenated hydantoins shown below in Table 1 were stirred in 3500 ml of distilled water. A sufficient quantity of the halogenated hydantoin was used in each run (1–3 g) to assure the presence of excess (undissolved) solids at the termination of the stirring period. A sample was then filtered to remove excess solids and analyzed for active halogen. The active halogen analysis for bromine and chlorine are expressed throughout in chlorine equivalents as Total $Cl^+$ (combined+free) and Free $Cl^+$.

TABLE 1

| | Ratio of Free to Total Halogen | | | | | |
|---|---|---|---|---|---|---|
| Run No. | Hydantoin Mole Ratio DMH | MEH | Percent Br | Percent Cl | Total $Cl^+$, ppm | Free $Cl^+$, ppm | Percent Free $Cl^+$ |
| 1 | 1 | — | 0 | 35.3 | 11.7 | 4.1 | 35 |
| 2 | 1 | — | 33.2 | 14.6 | 5.8 | 3.1 | 54 |
| 3 | 1 | — | 53.8 | 0 | 7.9 | 6.3 | 80 |
| 4 | — | 1 | 45.8 | 3.3 | 25.0 | 17.5 | 70 |

TABLE 1-continued

| | | | | Ratio of Free to Total Halogen | | | |
|---|---|---|---|---|---|---|---|
| Run No. | Hydantoin Mole Ratio | | Percent Br | Percent Cl | Total Cl+, ppm | Free Cl+, ppm | Percent Free Cl+ |
| | DMH | MEH | | | | | |
| 5 | 0.8 | 0.2 | 52.3 | 0.2 | 5.9 | 5.2 | 88 |
| 6 | 0.8 | 0.2 | 54.2 | 0.2 | 6.2 | 5.5 | 88 |
| 7 | 0.8 | 0.2 | 33.4 | 14.0 | 5.8 | 3.1 | 54 |
| 8 | 0.8 | 0.2 | 27.2 | 18.0 | 8.7 | 4.0 | 46 |

The results in Table 1 show that in the case of fully chlorinated dimethylhydantoin (DMH), only 35% of the total chlorine exists as free chlorine (Run No. 1). However, when fully brominated, the free Cl+ (equivalent) increases to 80% of the total Cl+ (Run No. 3). Not unexpectedly, the intermediate bromochloro DMH yields the intermediate value of 54% (Run No. 2).

In Run No. 4, highly brominated methylethylhydantoin (MEH) was prepared and tested. Predictably, the ratio of free Cl+ declined to 70%, correlatable to its lower bromine content as compared with dibromodimethylhydantoin (DBDMH). However, the concentration of total Cl+ increased significantly, a desirable result in view of the intended applications.

In Runs No. 5, 6, 7 and 8, mixtures of DMH (0.8 mole) and MEH (0.2 mole) were bromo-chlorinated by adding the desired amount of bromine, and then completing the halogenation of the mixed hydantoins with chlorine. Again, perfect correlation was obtained between the bromine content of the hydantoin and the ratio of free Cl+ irrespective of the parent hydantoin. The concentration of total Cl+ decreased because of the high DMH content of the mixed hydantoins.

Therefore, by selecting the appropriate halogenated hydantoin, it is possible to achieve the level of "free halogen" required by the intended use.

EXAMPLE TWO

Addition of Magnesium Oxide to Granular Halohydantoin

In an effort to determine the effect of magnesium oxide on the rate of solubilization of halohydantoins, the following procedures were carried out using bromochlorinated methylethylhydantoin containing 35.7% Br and 9.5% Cl.

The bromochloro methylethylhydantoin was evaluated (1) without additive and (2) with 2.5% MgO in granular form. The granules were made by compressing the powder on continuous compacting rolls, passing the compressed material through a granulator, screening the fractured compacted solids, and separating the granules which passed through a 20 mesh screen and collected on a 40 mesh screen.

The rate of solubility was determined by adding a 10 gram portion of the granules to 500 ml of water in a rotary flask to provide for gentle agitation and then taking an aliquot at the time intervals shown in Table 2, filtering to remove any suspended solids, and then analyzing for total Cl+ and free Cl+.

Table 2 below summarizes the results by expressing the percentage increase in total Cl+ and free Cl+ resulting from the addition of 2.5% MgO. It is clear that MgO increases the rate of dissolution significantly. As compared with the control, there is a 44.3% increase of total Cl+, and a 36.2% increase in free Cl+ at the 5 minute interval. Equilibrium is achieved at the 60 minute interval. This increase in the rate of dissolution is highly desirable for such purposes as toilet bowl cleansing where effectiveness must be maintained under more frequent use conditions.

TABLE 2

| | Rate of Granule Solubilization | | | | | |
|---|---|---|---|---|---|---|
| | 5 Minute | | 15 Minutes | | 60 Minutes | |
| Additive | Total Cl+ ppm | Free Cl+ ppm | Total Cl+ ppm | Free Cl+ ppm | Total Cl+ ppm | Free Cl+ ppm |
| 0 | 523 | 362 | 1315 | 850 | 1733 | 1086 |
| 2.5% MgO | 771 | 491 | 1457 | 922 | 1820 | 1134 |
| Percent Increase | 47.4 | 35.6 | 10.8 | 8.5 | 5.6 | 4.4 |

EXAMPLE THREE

Addition of Magnesium Oxide To Powdered Halohydantoin

Using the halohydantoin of Example Two in powdered form, the effect of adding magnesium oxide thereto was evaluated to determine the time needed to achieve equilibrium. Ten grams of the powder sample were added to 500 ml of water and agitated for the interval indicated in Table 3. The free and total halogen was measured as in Example Two above. The results are set forth in Table 3 below.

TABLE 3

| | Rate of Powder Dissolution | | |
|---|---|---|---|
| Additive | Time (hrs) | Total Cl+, ppm | Free Cl+, ppm |
| 0 | 4 | 1874 | 1152 |
| 0 | 2½ | 1824 | 1133 |
| 0 | 1 | 1835 | 1163 |
| 2.5% MgO | 4 | 2101 | 1279 |
| 2.5% MgO | 2½ | 2099 | 1236 |
| 2.5% MgO | 1 | 1887 | 1144 |

The results shown in Table 3 reveal that equilibrium is reached in about one hour. Equilibrium is achieved rapidly because of the high surface area of the powder and granules.

EXAMPLE FOUR (COMPARATIVE)

Effect of Pressure And Dilution On Dissolution of Briquettes and Tablets

Using powdered halogenated methylethylhydantoin (34.9% Br and 10.3% Cl) the effect of tableting pressure and dilution on the rate of dissolution was studied.

Tablets were made by compressing 10 grams of the powder sample in a Carver press. The dimensions of the tablet were 1⅛″ diameter, ¼″ thickness.

The tablets were immersed in water for 1 hour without agitation and then the solutions were analyzed. The following two variables were studied:
1. The pressure applied to compress the powder into tablets (500 psi and 20,000 psi).
2. The volume of water used to determine solubility (20, 40, 60, and 80 ml).

The results obtained are summarized in Table 4.

TABLE 4

| | Effect of Pressure and Dilution | | | |
|---|---|---|---|---|
| Ml of Water | 500 psi Tablets | | 20,000 psi Tablets | |
| | Free Cl+ | Total Cl+ | Free Cl+ | Total Cl+ |
| 20 | 422 | 906 | 337 | 748 |
| 40 | 218 | 452 | 191 | 380 |
| 60 | 146 | 292 | 122 | 246 |

TABLE 4-continued

| | Effect of Pressure and Dilution | | | |
|---|---|---|---|---|
| Ml of | 500 psi Tablets | | 20,000 psi Tablets | |
| Water | Free Cl+ | Total Cl+ | Free Cl+ | Total Cl+ |
| 80 | 106 | 237 | 80 | 162 |

The results show that tablets do not dissolve rapidly and that increasing the pressure during tablet formation decreases the rate of dissolution. As expected, the concentration declines with dilution, showing that equilibrium was not achieved during the one hour exposure. Had equilibrium been achieved, the concentration at each dilution would have been the same.

EXAMPLE FIVE

Comparison Of Various Additives On Dissolution Rate Of Halohydantoin

The tableting procedure of Example Four was selected as a means of determining the influence of a variety of additives on accelerating the rate of dissolution. The test comprised of placing 10 g tablets of the test materials in a breaker containing 60 ml of water and gently agitating at room temperature for one hour. The resulting solution was then analyzed for total Cl+ and free Cl+. The results are shown in Table 5 below.

TABLE 5

| | Effect Of Additives On The Rate Of Dissolution Of Bromochlorinated Ethylmethylhydantoin | | | | | | | |
|---|---|---|---|---|---|---|---|---|
| | Agitated | | | | Non-Agitated | | | |
| | Total Cl+ | Free Cl+ | % Increase | | Total Cl+ | Free Cl+ | % Increase | |
| Additive | ppm | ppm | Total | Free | ppm | ppm | Total | Free |
| 0 | 855 | 563 | — | — | 233 | 154 | — | — |
| 1.0% MgO | 1017 | 656 | 19 | 17 | 259 | 156 | 11 | 1 |
| 2.5% MgO | 1041 | 686 | 22 | 22 | 292 | 180 | 25 | 17 |
| 5.0% MgO | 1065 | 698 | 25 | 24 | 314 | 192 | 35 | 25 |
| 1% Al(OH)3 | 836 | 590 | −2 | 5 | 235 | 148 | 1 | −4 |
| 2.5% Al(OH)3 | 812 | 470 | −5 | −1 | 208 | 136 | −11 | −12 |
| 2.5% Ba(OH)2 | 1017 | 645 | 19 | 15 | 257 | 153 | 10 | −1 |
| 2.5% Na2CO3 | 1010 | 654 | 15 | 16 | 256 | 156 | 10 | 1 |
| 5% DMH | 1261 | 830 | 41 | 42 | — | — | — | — |
| 20% DMH | 1322 | 871 | 50 | 51 | — | — | — | — |

The results show that magnesium oxide, barium hydroxide, and sodium carbonate increase the rate of solubilization, while aluminum hydroxide decreases the rate of solubilization. A comparable series of measurements were made without agitation; while the total amount dissolved was less than in the stirred beaker, the same relative results were obtained. Increasing the rate of solubilization without agitation is of great value in toilet bowl cleanser applications because bleaching and disinfecting effectiveness is maintained despite frequent flushing.

The most significant increase was obtained by the addition of 5% and 20% dimethylhydantoin which provided for a 50% increase in total Cl+ and free Cl+.

EXAMPLE SIX

Solubilizing Effect Of DMH

To exemplify further the effect of DMH and magnesium oxide on the solubilization of halohydantoins, a halohydantoin containing 20.8% Br, and 22.6% Cl prepared from a mixture of 0.8 mole of DMH and 0.2 mole of MEH by bromochlorination was selected. Tablets containing the additive were placed in a beaker containing 60 ml of water and gently agitated for 1 hour and then analyzed for total Cl+ and free Cl+. The results are summarized in Table 6 below.

TABLE 6

| | Solubilizing Effect of Dimethylhydantoin | | | |
|---|---|---|---|---|
| | | Increase, % | | |
| Additive | Total Cl+ | Total Cl+ | Free Cl+ | Increase % Free Cl+ |
| 0 | 442 | 0 | 201 | — |
| 5% DMH | 634 | 43 | 244 | 21 |
| 20% DMH | 1384 | 213 | 517 | 157 |
| 17.5% DMH + 2.5 MgO | 1531 | 246 | 474 | 136 |

The results show a remarkable increase in both the total Cl+ and free Cl+.

EXAMPLE SEVEN

Solubilizing Effect Of MgO on Briquettes

The influence of magnesium oxide on the rate of solubilization of briquettes was also studied. 11 g briquettes were fabricated and their solubility determined by placing them in a beaker containing water and then analyzing for ppm of total Cl+ and ppm of free Cl+ after 1 hour. The briquettes were formed in commercial compacting rolls. The volume of water used for the solubility tests was varied—20, 40, 60, and 80ml/one 11 g briquette. The halohydantoin used to make the briquettes was a bromochlorinated ethylmethylhydantoin containing 34.9% Br, and 10.3% Cl. The results are summarized in Table 7 below.

TABLE 7

| | Effect Of MgO On Solubilization Of Briquettes | | | | | |
|---|---|---|---|---|---|---|
| | No Additive | | 1% MgO | | 2.5% MgO | |
| Dilution ml of H2O | Free Cl+ | Total Cl+ | Free Cl+ | Total Cl+ | Free Cl+ | Total Cl+ |
| 20 | 492 | 896 | 576 | 1191 | 624 | 1092 |
| 40 | 262 | 476 | 334 | 614 | 371 | 615 |
| 60 | 179 | 307 | 217 | 411 | 245 | 394 |
| 80 | 141 | 249 | 167 | 194 | 192 | 307 |

The results shown in Table 7 reveal that both total and free Cl+ are increased as the result of the addition of MgO.

EXAMPLE EIGHT

Toilet Bowl Application

Four ten gram tablets of each of the bromochlorinated ethylmethylhydantoin compositions of Example Five containing the additives noted below are charged to passive dosing dispersers sold in the U.S. under the brand name TANK II (Boyle-Midway). The dispensers are then placed in the tank reservoir of separate American Standard flush toilets:

Additive 1.0% MgO
2.5% MgO
1.05% MgO
10.0% MgO
2.5% Ba(OH$_2$)
2.5% Na$_2$CO$_3$
5.0% DMH
20.0% DMH
10.0% DEH
10.0% MEH.

In each instance the compositions provide satisfactory sanitizing and bleaching of the toilet bowl for extended flushes.

EXAMPLE NINE

Tablet Life 50 grams of tablets prepared in a Carver press from a mixture of 97.5 percent dibromomethylethylhydantoin and 2.5 percent magnesium oxide were placed in the tank reservoir of a flush toilet having an average tank temperature of 20° C. and pH of about 9.0. The tank was flushed each hour. Both the free available and total halogen (expressed as chlorine) were measured at various intervals. After 260 flushes, 18% of the material remained.

EXAMPLE TEN

Briquette Life 52 grams of briquettes composed of 75% dibromomethylethylhydantoin and 25% dimethyl hydantoin were placed in the tank of a flush toilet as in Example Nine. The halogen content was measured after various hourly flush intervals. After 134 flushes, only 63% of the material was consumed.

The foregoing examples clearly demonstrate the potentiating effect of the solubilizing agents of the present invention on the rate of generating both total and free halogen in aqueous solutions of halogenated hydantoins. It will be appreciated that the present invention as claimed below is not limited to the specific embodiment described herein. In addition, the invention may comprise, consist or consist essentially of the materials and procedures recited herein.

What is claimed is:

1. A composition, suitable for toilet bowl cleaning, which comprises a halogenated hydantoin of the formula:

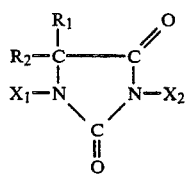

wherein X$_1$ and X$_2$ independently are chlorine or bromine, R$_1$ and R$_2$ independently are methyl or ethyl; and a solubilizing agent selected from the group consisting of magnesium oxide, barium hydroxide, and mixtures thereof, which is present in an amount sufficient to increase the rate of solubility of the hydantoin when placed in an aqueous environment.

2. The composition of claim 1 in the form of powder or granules.

3. The composition of claim 1 in the form of tablets or briquettes.

4. The composition of claim 1, wherein R$_1$ is ethyl and R$_2$ is methyl.

5. The composition of claim 1 wherein X$_1$ and X$_2$ are different.

6. The composition of claim 1 containing from about 0.5 to 10 percent by weight of magnesium oxide as the solubilizing agent.

7. The composition of claim 6 wherein magnesium oxide is present in an amount ranging from about 1 to 5 percent by weight.

8. The composition of claim 7 containing about 2.5 percent magnesium oxide.

9. The composition of claim 5 containing about 2.5 percent magnesium oxide.

10. The composition of claim 1 further containing up to an equal molar amount of 5,5-dialkyl substituted hydantoin selected from the group consisting of dimethylhydantoin, methylethylhydantoin and diethylhydantoin, based on the halogenated hydantoin.

11. The composition of claim 10 wherein the hydantoin is present in an amount ranging from about 5 to 20 percent by weight.

12. The composition of claim 1 containing from 0.5 to 10 percent by weight of a solubilizing agent of barium hydroxide.

13. The composition of claim 12 wherein the solubilizing agent is present in an amount ranging from about 1 to about 5 percent by weight.

14. A method for the cleansing of a flush toilet having a tank reservoir for containing a quantity of water which comprises adding to the reservoir the composition of claim 1.

15. A method according to claim 14 wherein the composition is added in dosage form through use of a passive dosing dispenser.

16. A method for the cleansing of a flush toilet having a tank reservoir for containing a quantity of water which comprises adding to the reservoir the composition of claim 1 in the form of tablets or briquettes.

17. A method of increasing the rate of solubility of a halogenated hydantoin in an aqueous solution, which comprises adding to said solution a halogenated hydantoin and a solubility agent selected from the group consisting of magnesium oxide, barium hydroxide, and mixtures thereof, in an amount sufficient to increase the rate of solubility of the halogenated hydantoin in the aqueous solution.

18. The method of claim 17 wherein said hydantoin has the formula:

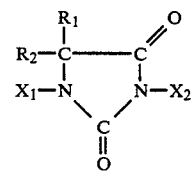

wherein X$_1$ and X$_2$ independently are chlorine or bromine; and R$_1$ and R$_2$ independently are methyl or ethyl.

19. The method of claim 18 wherein $X_1$ and $X_2$ are different and $R_1$ and $R_2$ are different.

20. The method of claim 18 wherein the solubility agent is selected from the group consisting of magnesium oxide, barium hydroxide, and mixtures thereof and is present in an amount ranging from about 0.5 to about 10 percent by weight based on the halogenated hydantoin.

21. The method of claim 18 wherein dimethyl hydantoin is present in an amount up to an equimolar amount based on the halogenated hydantoin.

22. The method of claim 21 wherein the amount of dimethyl hydantoin ranges from about 5 to about 25 percent by weight.

23. In a dispenser designed for placement in the water of a flush tank reservoir of a toilet which comprises a dispensing means which contains a composition which is effective in cleansing the bowl of the toilet when dispensed during flushing, the improvement wherein said composition in said dispensing means comprises the solid composition of claim 1.

* * * * *